(12) United States Patent  
Kim et al.

(10) Patent No.: US 12,364,417 B2  
(45) Date of Patent: Jul. 22, 2025

(54) ELECTRONIC DEVICE AND METHOD OF ESTIMATING BIOINFORMATION

(71) Applicant: SAMSUNG ELECTRONICS CO., LTD., Suwon-si (KR)

(72) Inventors: Yoon Jae Kim, Seoul (KR); Hyun Seok Moon, Hwaseong-si (KR); Jin Young Park, Hwaseong-si (KR); Kun Sun Eom, Yongin-si (KR); Myoung Hoon Jung, Bucheon-si (KR); Jeong Eun Hwang, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 491 days.

(21) Appl. No.: 17/696,077

(22) Filed: Mar. 16, 2022

(65) Prior Publication Data

US 2023/0157593 A1 May 25, 2023

(30) Foreign Application Priority Data

Nov. 19, 2021 (KR) .................. 10-2021-0160376

(51) Int. Cl.
*A61B 5/1455* (2006.01)
*A61B 5/00* (2006.01)
*A61B 5/0205* (2006.01)
*A61B 5/021* (2006.01)
*A61B 5/145* (2006.01)

(52) U.S. Cl.
CPC .......... *A61B 5/1455* (2013.01); *A61B 5/0205* (2013.01); *A61B 5/021* (2013.01); *A61B 5/14546* (2013.01); *A61B 5/748* (2013.01)

(58) Field of Classification Search
None
See application file for complete search history.

(56) References Cited

U.S. PATENT DOCUMENTS

| | | | |
|---|---|---|---|
| 7,365,839 B2 | 4/2008 | Ferguson et al. | |
| 8,260,402 B2 | 9/2012 | Ermakov et al. | |
| 9,795,309 B2 | 10/2017 | Shim et al. | |
| 9,814,417 B2 | 11/2017 | Sharifzadeh et al. | |
| 11,553,845 B2 * | 1/2023 | Lee | A61B 5/7278 |
| 2009/0327942 A1 * | 12/2009 | Eldridge | G06F 8/34 |
| | | | 715/771 |
| 2010/0030480 A1 | 2/2010 | Wolfgang | |

(Continued)

FOREIGN PATENT DOCUMENTS

| KR | 10-2009-0040252 A | 4/2009 |
|---|---|---|
| KR | 10-2011-0122120 A | 11/2011 |

(Continued)

*Primary Examiner* — Benjamin J Klein
*Assistant Examiner* — Willow Grace Welch
(74) *Attorney, Agent, or Firm* — Sughrue Mion, PLLC

(57) ABSTRACT

An electronic device according to one aspect may include a main body, a sensor part disposed on one surface of the main body and configured to detect a light signal of an object, a first output interface comprising a light emitter disposed on one surface of the main body and configured to guide a user through a measurement operation by controlling a light-emitting mode of the light emitter, and a processor configured to control the first output interface according to the measurement operation and estimate the user's bioinformation based on a result of detecting the light signal by the sensor part.

19 Claims, 15 Drawing Sheets

(56) References Cited

U.S. PATENT DOCUMENTS

| | | |
|---|---|---|
| 2014/0058224 A1 | 2/2014 | Gellermann et al. |
| 2017/0293740 A1 | 10/2017 | Xing |
| 2020/0029873 A1 | 1/2020 | Park et al. |
| 2020/0085323 A1* | 3/2020 | Lee .................. A61B 5/02108 |
| 2020/0196935 A1* | 6/2020 | Eom .................. A61B 5/443 |
| 2020/0217792 A1 | 7/2020 | Magnussen et al. |
| 2020/0378890 A1 | 12/2020 | Lee |
| 2021/0036046 A1 | 2/2021 | Kwon et al. |
| 2021/0113087 A1 | 4/2021 | Jang et al. |
| 2021/0121102 A1 | 4/2021 | Lee et al. |
| 2021/0172867 A1 | 6/2021 | Park et al. |
| 2022/0133241 A1* | 5/2022 | Jones .................. A61B 5/1032 600/485 |

FOREIGN PATENT DOCUMENTS

| | | |
|---|---|---|
| KR | 10-2015-0081251 A | 7/2015 |
| KR | 10-2015-0142310 A | 12/2015 |
| KR | 10-2020-0012597 A | 2/2020 |
| KR | 10-2020-0137103 A | 12/2020 |
| KR | 10-2021-0014559 A | 2/2021 |
| KR | 10-2021-0047540 A | 4/2021 |
| KR | 10-2021-0050967 A | 5/2021 |
| KR | 10-2021-0069945 A | 6/2021 |

\* cited by examiner

ELECTRONIC DEVICE AND METHOD OF ESTIMATING BIOINFORMATION

CROSS-REFERENCE TO RELATED APPLICATION(S)

This application claims the benefit under 35 U.S.C. § 119(a) of Korean Patent Application No. 10-2021-0160376, filed on Nov. 19, 2021, in the Korean Intellectual Property Office, the entire disclosure of which is incorporated herein by reference for all purposes.

BACKGROUND

1. Field

The following description relates to an electronic device for estimating biological information ("bioinformation") in a non-invasive manner and a method of estimating bioinformation.

2. Description of Related Art

With the aging population, increased medical costs, and a lack of medical personnel for specialized medical services, research is being actively conducted on information technology (IT)-medical convergence technologies, in which IT technology and medical technology are combined. Particularly, monitoring of a health condition of a human body may not be limited to places such as hospitals, but is expanded by mobile healthcare fields that may monitor a user's health condition anywhere (e.g., at home or office on in transit from one place to another place) and anytime in daily life. Some examples of biological signals (biosignals), which indicate the health condition of individuals, may include an electrocardiography (ECG) signal, a photoplethysmography (PPG) signal, an electromyography (EMG) signal, and the like, and various biosignal sensors are being developed to measure the biosignals in daily life.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

In one general aspect, there is provided an electronic device including a main body, a sensor part disposed on one surface of the main body and configured to detect a light signal of an object, a first output interface including a light emitter disposed on one surface of the main body and configured to guide a user through a measurement operation by controlling a light-emitting mode of the light emitter, and a processor configured to control the first output interface according to the measurement operation and estimate the user's bioinformation based on a result of detecting the light signal by the sensor part.

The measurement operation may include a measurement start operation, a measurement development operation, and a measurement completion operation.

When the light emitter is configured with one light emitting diode (LED), the first output interface may adjust a blinking pattern of the LED in each measurement operation.

When the light emitter is configured with a plurality of LEDs having different wavelengths, the first output interface may adjust at least one of a blinking pattern and a color pattern of each LED in each measurement operation.

The measurement operation may further include a pressure operation, and the first output interface, when guiding the pressure operation, may guide the user by adjusting at least one of a blinking pattern and a color pattern of an LED included in the light emitter.

The processor may determine a degree of pressure by the user based on a change in absorbance at a predetermined wavelength range.

The first output interface may guide the measurement operation by adjusting at least one of a blinking speed, brightness, color type, and color density of the LED in comparison with a starting time point of the pressure operation according to the determined degree of pressure.

The processor may determine whether the determined degree of pressure reaches an appropriate level of pressure, and the first output interface, when the processor determines that the degree of pressure does not reach the appropriate level of pressure, may guide the user through additional pressure by increasing a blinking speed of the LED, increasing brightness of the LED, adjusting color of the LED, or increasing density of color of the LED.

The sensor part may include a light source configured to emit light to the object and a detector configured to detect a light signal based on light scattered or reflected from the object, wherein a wavelength of the light emitted by the light source may be 400 nm or more and 600 nm or less and the bioinformation may be an antioxidant index.

The electronic device may further include a second output interface disposed on the other surface of the main body and configured to provide instructions on a guiding method of the first output interface to the user before the light signal is detected.

The second output interface may output graphical objects regarding explanatory information on a light-emitting mode for each operation together with the light-emitting mode of the first output interface for each operation.

The second output interface may output a graphical object for the user to skip the instructions, and output a text message for guiding the user to start a measurement when the user selects the graphical object.

In another general aspect, there is provided a method of estimating bioinformation including guiding a user through a measurement operation by adjusting a light-emitting mode of a light emitter disposed on one surface of a main body, detecting a light signal of an object, and estimating bioinformation of the user based on a result of detecting the light signal.

The measurement operation may include a measurement start operation, a measurement development operation, and a measurement completion operation.

The guiding of the user through the measurement operation may include, when the light emitter is configured with one LED, adjusting a blinking pattern of the LED in each measurement operation.

The guiding of the user through the measurement operation may include, when the light emitter is configured with a plurality of LEDs having different wavelengths from each other, adjusting at least one of a blinking pattern and a color pattern of each LED in each measurement operation.

The measuring operation may further include a pressure operation, and the guiding of the user through the measurement operation may include, when guiding the pressure operation, adjusting at least one of a blinking pattern and a color pattern of an LED included in the light emitter.

The method may further include determining a degree of pressure by the user based on a change in absorbance at a predetermined wavelength range.

The guiding of the user through the measurement operation may include guiding the measurement operation by adjusting at least one of a blinking speed, brightness, color type, and color density of the LED in comparison with a starting time point of the pressure operation according to the determined degree of pressure.

The method may further include providing instructions on a method of guiding the user through the measurement operation by adjusting a light-emitting mode of the light emitter to the user before detecting the light signal.

In this case, the guiding of the user through the measurement operation may include outputting a graphical object for the user to skip the instructions and outputting a text message for guiding the user to start a measurement when the user selects the graphical object.

Other features and aspects will be apparent from the following detailed description, the drawings, and the claims.

Figure 1:
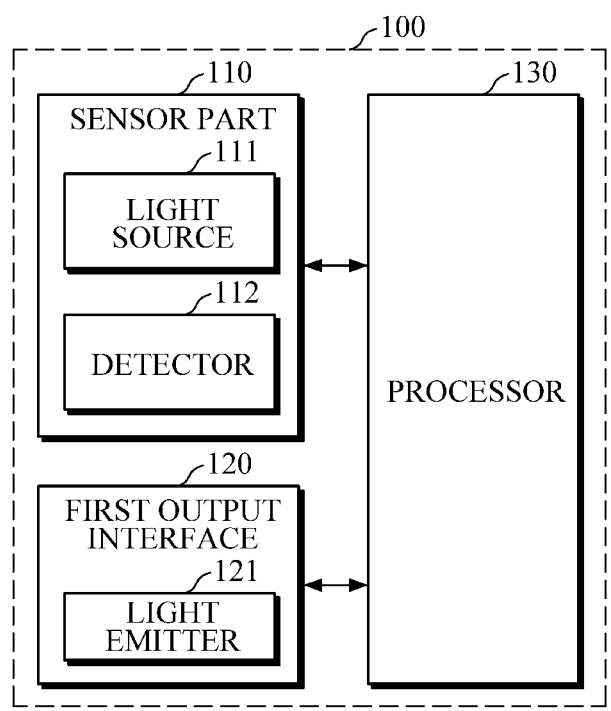
FIG. 1 is a block diagram illustrating an electronic device according to an exemplary embodiment.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

Details of exemplary embodiments are provided in the following detailed description with reference to the accompanying drawings. The disclosure may be understood more readily by reference to the following detailed description of exemplary embodiments and the accompanying drawings. The disclosure may, however, be embodied in many different forms and should not be construed as being limited to the embodiments set forth herein. Rather, these embodiments are provided so that the disclosure will be thorough and complete and will fully convey the concept of the invention to those skilled in the art, and the disclosure will only be defined by the appended claims. Like reference numerals refer to like elements throughout the specification.

It will be understood that, although the terms first, second, etc. may be used herein to describe various elements, these elements should not be limited by these terms. These terms are only used to distinguish one element from another. Also, the singular forms are intended to include the plural forms as well, unless the context clearly indicates otherwise. In the specification, unless explicitly described to the contrary, the word "comprise" and variations such as "comprises" or "comprising," will be understood to imply the inclusion of stated elements but not the exclusion of any other elements. Terms such as "unit" and "module" denote units that process at least one function or operation, and they may be implemented by using hardware, software, or a combination of hardware and software.

Hereinafter, embodiments of an electronic device and a method for estimating bioinformation will be described with reference to the drawings.

FIG. 1 is a block diagram illustrating an electronic device according to an exemplary embodiment. The electronic device 100 includes at least one wearable device such as a wristwatch type, a bracelet type, a wristband type, a ring type, a glass-type, and a hairband type, a smart phone, a mobile phone, a wrist watch, and various medical devices (shortwave infrared camera, long wave infrared cameras, etc.) and combinations thereof.

Referring to FIG. 1, the electronic device 100 includes a sensor part 110, a first output interface 120, and a processor 130.

The electronic device 100 may estimate bioinformation of a user based on a measured biosignal. In this case, the bioinformation may include antioxidant index, blood pressure, blood sugar, lactic acid, alcohol, cholesterol, triglyceride, and the like, but is not limited thereto. Hereinafter, for convenience of description, antioxidant index will be taken as an example of the bioinformation.

The sensor part 110 may be disposed on one surface of the main body of the electronic device 100. In this case, when the electronic device 100 is a wrist watch type wearable device, the sensor part 110 may be disposed on a rear surface of the main body of the watch, but is not limited thereto.

The sensor part 110 may measure a biosignal of an object of the user. Examples of the biosignal may include a photoplethysmography (PPG) signal. However, the examples of the biosignal are not limited thereto, and the sensor part 110 may measure other biosignals, such as ECG signals and the like.

In this case, the object may be a region of a wrist surface adjacent to the radial artery, which is an upper area of the wrist where the capillary blood or venous blood passes through, or a body part with a high blood vessel density, e.g., a finger, a toe, an earlobe, etc.

The sensor part 110 may include a light source 111 configured to emit light toward the object, and a detector 112 configured to detect light scattered or reflected by the body tissue of the object that is irradiated by the light source 111.

In this case, the light source 111 may include at least one of a light emitting diode (LED), a laser diode, or a phosphor, but is not limited thereto. The detector 112 may include a photodiode, a photo transistor, a photodiode array, a phototransistor array, an image sensor (e.g., a complementary metal oxide semiconductor (CMOS) image sensor), etc. The light source 111 may be a plurality of light sources configured to emit light having the same wavelength or emit light having different wavelengths from each other. For example, the plurality of light sources may emit light of green wavelength, blue wavelength, red wavelength, infrared wavelength, etc., but are not limited thereto. the detector 112 may be a plurality of detectors disposed at different distances from the light source 111.

Figure 2A:
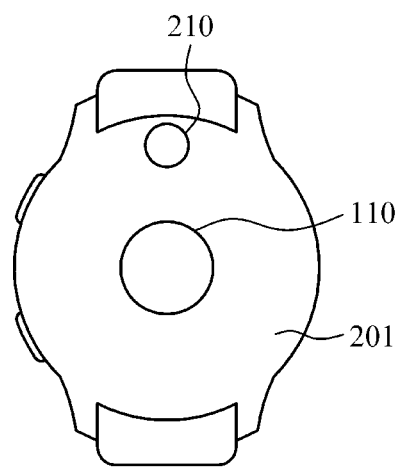
FIG. 2A is a diagram illustrating a structure of a sensor part according to an exemplary embodiment.

FIG. 2A is a diagram illustrating a structure of a sensor part according to an exemplary embodiment. Referring to FIG. 2A, the sensor part 110 may have the light source 111 having a plurality of the light sources disposed at the center thereof, and the detector 112 having a plurality of detectors disposed in a concentric circle at the periphery thereof. FIG. 2A illustrates that there are eight detectors in the detector 112, but the present disclosure is not limited thereto and the number of detectors in the detector 112 may be varied without limitation.

The sensor part 110 may further include an additional configuration necessary for biosignal measurement. For example, additional configurations, such as an amplifier configured to amplify an electrical signal output by the detector that has detected by the light signal, or an analog-to-digital converter configured to convert an electrical signal output by a detector, or an electrical signal output by the amplifier, into a digital signal, may be further included in the light sensor 110. In addition, in the case where the sensor part 110 measures an ECG signal, the sensor part 110 may include a plurality of electrodes.

The first output interface 120 may include a light emitter 121, and may guide a user through a measurement operation using the light emitter 121.

The sensor part 110 may be disposed at or on one surface of the main body of the electronic device 100. In this case, the light emitter 121 may be disposed at or on the same surface as the sensor part 110. For example, in the case where the electronic device 100 is a wrist watch type wearable device, the sensor part 110 and the light emitter 121 may be all disposed on the rear surface of the main body of the watch. However, the present disclosure is not limited thereto such that the sensor part 110 may be disposed on the rear surface of the main body of the watch and the light emitter 121 may be disposed on the side surface of the watch.

In the case where the sensor part 110 is disposed on the rear surface of the main body and a display configured to visually guide the user through a bioinformation measurement process is disposed on the front surface of the main body, it may be somewhat inconvenient for the user to press a sensor disposed on the rear surface with the object (e.g., a finger) and at the same time check the bioinformation measurement process through the display disposed on the front surface of the main body in a state in which the user turns the main body over so that the rear surface of the main body is visible for measuring the bioinformation. Therefore, when the first output interface 120 that guides the user for the measurement operation is disposed on the same surface as the sensor part 110, for example, on the rear surface of the wrist type wearable device, the user does not need to check the display on the front surface during the measurement, so that the convenience of the user can be improved.

The light emitter 121 may include at least one light emitting diode (LED). In this case, when the light emitter 121 includes a plurality of LEDs, the LEDs may have different wavelengths from each other. For example, each LED may be configured to have a different one of blue, red, yellow, orange, and green wavelengths. The shape of the light emitter 121 disposed in the electronic device 100 will be described in detail with reference to FIGS. 2B to 2D.

Figure 2B:
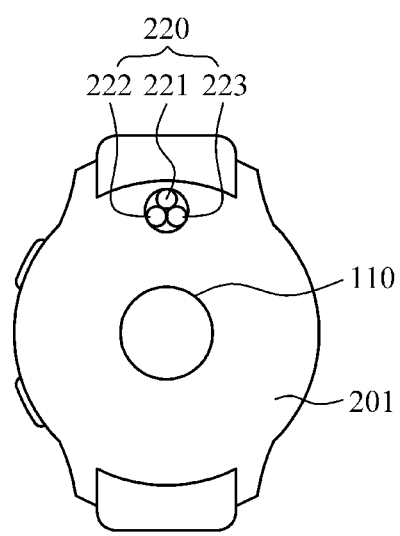
FIGS. 2B to 2D are diagrams illustrating a light emitter according to an exemplary embodiment.
Figure 2C:
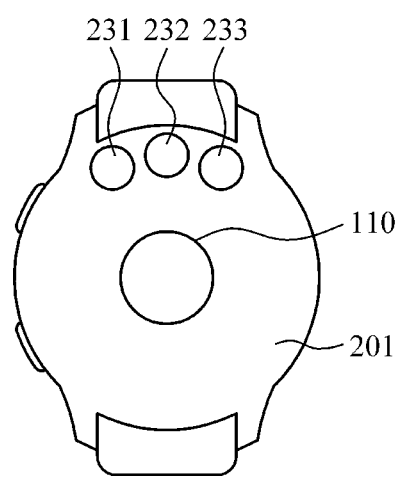
Figure 2D:
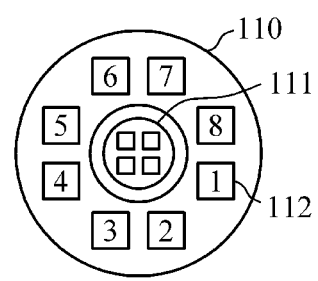

FIGS. 2B to 2D are diagrams illustrating a light emitter according to an exemplary embodiment. FIGS. 2B to 2D illustrate a main body 201, the sensor part 110, and light emitters 210, 220, 231, 232, and 233 of the electronic device. In FIGS. 2B to 2D, the sensor part 110 and the light emitters 210, 220, 231, 232, and 233 are illustrated as being disposed on the rear surface of the main body 201 of the wrist watch type wearable device, but as described above, the type of the electronic device and the positions at which the sensor part 110 and the light emitters 210, 220, 231, 232, and 233 are disposed are not limited thereto.

FIG. 2B illustrates an example in which the light emitter is configured with one LED 210, and FIGS. 2C and 2D illustrates an example in which the light emitter is configured with a plurality of LEDs 220, 231, 232, and 233 having different wavelengths from each other. In this case, FIG. 2C illustrates an example in which a plurality of LEDs 221, 222, and 223 form an LED module 220, and FIG. 2D illustrates an example in which a plurality of LEDs are separately disposed without forming an LED module.

FIGS. 2B to 2D illustrate an example in which the light emitters 210, 220, 231, 232, and 233 are disposed above the sensor part 110, but the present disclosure is not limited thereto such that the light emitters 210, 220, 231, 232, and 233 may be disposed below or on the side of the sensor part 110 on the rear surface of the main body 201. In addition, when the plurality of LEDs do not form a module, the disposed positions of each LED may be different from each other, such as some of the LEDs 231, 232, and 233 being disposed above the sensor part 110 and the others being disposed below or on the side of the sensor part 110, etc.

In FIGS. 2C and 2D, the light emitters 220, 231, 232, and 233 are illustrated as including three LEDs having different wavelengths, but are not limited thereto, and the number of LEDs included in the light emitters 220, 231, 232, and 233 may be varied without limitation.

Referring back to FIG. 1, the processor 130 may be connected to the sensor part 110 and the first output interface 120 electrically, mechanically, or through wired/wireless communication.

The processor 130 may control the first output interface 120 according to a measurement operation. In this case, the first output interface 120 may guide the user through the measurement operation by controlling a light-emitting mode of the light emitter 121. In this case, the measurement operation may include a measurement start operation, a measurement development operation, and a measurement completion operation.

The measurement start operation may refer to an operation that takes place before detection of a biosignal, that is, an operation in which the first output interface 120 guides the user to bring an object into contact with the sensor part 110. The measurement development operation may refer to an operation in which the sensor part 110 detects the user's biosignal using the light source 111 and the detector 112 after the object is in contact with the sensor part 110. The measurement completion operation may refer to an operation after the sensor part 110 completes the detection of the biosignal.

In the case where the light emitter 121 is configured with one LED as illustrated in FIG. 2B, the first output interface 120 may adjust a blinking pattern of the LED in each measurement operation. In this case, the blinking pattern may be determined variously by combining the on/off, brightness control, blinking speed, and the like of the LED. Table 1 below shows examples of the blinking pattern of the LED in each measurement operation, but the present disclosure is not limited thereto.

TABLE 1

|  | Measurement start operation | Measurement development operation | Measurement completion operation |
| --- | --- | --- | --- |
| Pattern 1 | LED ON | LED blinking | LED OFF |
| Pattern 2 | LED blinking | LED ON |  |
| Pattern 3 | LED OFF | LED ON |  |
| Pattern 4 | LED OFF | LED blinking |  |

In one example, referring to pattern 1, the first output interface 120 may turn on the LED at a first brightness when guiding the user through the measurement start operation, control the LED to blink at a predetermined blinking speed when guiding the user through the measurement development operation, and turn off the LED when guiding the user through the measurement completion operation. As a modification of pattern 1, the LED may be turned back on in the measurement completion operation. For example, the brightness at which the LED is turned on in the measurement start operation may be different from the brightness at which the LED is turned on in the measurement completion operation. For instance, the brightness of the LED in the measurement completion operation may be brighter, or the brightness of the LED in the measurement start operation may be brighter.

In another example, the first output interface 120 may turn on the LED at a first brightness when guiding the user through the measurement start operation, increase the brightness of the LED to a second brightness that is brighter than the first brightness when guiding the user through the measurement development operation, and turn off the LED when guiding the user through the measurement completion operation. However, the present disclosure is not limited thereto, and the blinking pattern for each operation may be varied without limitation.

In the case where the light emitter 121 is configured with a plurality of LEDs having different wavelengths from each other as illustrated in FIGS. 2C and 2D, the first output interface 120 may adjust the blinking pattern and/or color pattern of the LEDs for each measurement operation. In this case, the color pattern may be determined variously by combining the colors, color density, etc. of the LEDs. Table 2 below shows examples of the operation-specific color pattern of the plurality of LEDs having different wavelengths from each other, but the present disclosure is not limited thereto.

TABLE 2

|  | Measurement start operation | Measurement development operation | Measurement completion operation |
| --- | --- | --- | --- |
| Pattern 1 | Wavelength 1 | Wavelength 2 | Wavelength 1 |
| Pattern 2 | Wavelength 1 | Wavelength 2 | Wavelength 3 |
| Pattern 3 | Wavelength 1 | Wavelength 2 | LED OFF |

In one example, referring to pattern 1, the first output interface 120 turns on the LED having a first wavelength when guiding the user through the measurement start operation, turn on the LED having a second wavelength when guiding the user through the measurement development operation, and turn on the LED having the first wavelength when guiding the user through the measurement completion operation.

In another example, referring to pattern 2, the first output interface 120 may turn on the LED having the first wavelength when guiding the measurement start operation, turn on the LED having the second wavelength when guiding the user through the measurement development operation, and turn on the LED having the third wavelength when guiding the user through the measurement completion operation.

In still another example, the first output interface 120 may turn on the LED having the first wavelength when guiding the user through the measurement start operation, control the LED having the first wavelength to blink at a predetermined blinking speed when guiding the user through the measurement development operation, and turn on the LED having the second wavelength when guiding the user through the measurement completion operation. However, the present disclosure is not limited thereto, and the blinking speed and/or color pattern for each operation may be varied without limitation.

In this case, when the first output interface 120 guides the user through the measurement start operation, the processor 130 may determine whether the object is located on the sensor part 110, and may guide the measurement development operation after the object is located on the sensor part 110.

In one example, the processor 130 may control the light source 111 to emit light to the object, and then may determine whether the object is located on the sensor part 110, based on the amount of light received by the detector 112. For example, when the amount of light received by the detector 112 exceeds a threshold, the processor 130 may determine that the object is located on the sensor part 110.

In another example, the processor 130 may control the light source 111 to emit light of different wavelengths, and then, when the difference in the amount of light of each wavelength received by the detector 112 does not exceed a threshold, may determine that the object is located on the sensor part 110.

In still another example, in the case where the sensor part 110 includes a plurality of detectors 112, the processor 130 may determine whether the object is located on the sensor part 110, based on the amount of light detected by each detector 112. For example, the processor 130 may calculate the absorbance for each detector photodiode (PD) and determine the contact position of the object based on the calculated absorbance.

For example, when the object is usually in contact with the upper side of the sensor part 110, the amount of reflected light detected by the detectors (e.g., detectors 1, 2, 3, and 4 in FIG. 2A) on the lower side of the sensor part 110 that is not in contact with the object (e.g., a finger) is relatively small, and thus may have stronger absorbance than the other detectors (e.g., detectors 5, 6, 7, and 8 in FIG. 2A). From this result, it may be determined that the object of the user is not located accurately on the sensor part 110 but is disposed towards the upper portion of the sensor part 110.

The measurement operation may further include a pressure operation, and the first output interface 120 may guide the user through the pressure operation by adjusting the blinking pattern and/or color pattern of the LED of the light emitter 121 when guiding the pressure operation. In this case, the pressure operation may refer to an operation between the measurement start operation in which the object presses the sensor part 110 with a predetermined force and the measurement development operation.

The processor 130 may determine the degree to which the user's object presses upon the sensor part 110.

In one example, the processor 130 may control the light source 111 to emit light of a predetermined wavelength range and thereafter, determine the degree of pressure by the user, based on the change in absorbance at the corresponding wavelength range. In this case, the predetermined wavelength range may be a wavelength range at which the degree of absorbance for blood is high, for example, 530 nm or more and 580 nm or less, but is not limited thereto.

For example, if the absorbance measured when the object gradually presses the sensor part 110 in the pressure operation is less than or equal to a predetermined threshold, the processor 130 may determine that the blood vessel is sufficiently occluded and determine that the degree of pressure by the object has reached an appropriate pressure.

Alternatively, the processor 130 may calculate a difference between the absorbance measured in a state in which the object is in contact with the sensor part 110, for example, pressed to a predetermined pressure or less, and the absorbance measured when the object applies a gradually increasing force to the sensor part 110 in the pressure operation, and when the calculated difference is greater than or equal to a predetermined threshold, the processor 130 may determine that the blood vessel is sufficiently occluded and determine that the degree of pressure by the object has reached an appropriate pressure.

Meanwhile, in the pressure operation, the processor 130 may measure a change in absorbance as the pressure is gradually increased from the starting point of the pressure, and may determine the degree of pressure according to the change in absorbance.

In another example, the processor 130 may determine the degree of pressure by the object based on a force sensor (not shown) that the electronic device 100 may include.

The first output interface 120 may guide the user by adjusting the blinking pattern and/or color pattern of the light emitter 121 according to the degree of pressure determined by the processor 130. In one example, the first output interface 120 may guide the user by adjusting the blinking pattern and/or color pattern of the LED in comparison with the starting time point of the pressure operation so as to correspond to the determined degree of pressure.

In another example, the processor 130 may determine whether the determined degree of pressure reaches an appropriate level of pressure as described above, and the first output interface 120 may inform the user on whether the determined appropriate level of pressure has been reached. For example, the first output interface 120 may inform the user that the appropriate pressure has been completed, or when the appropriate level of pressure has not been reached, may guide the user through additional pressure.

Examples in which the first output interface 120 guides the user by adjusting the blinking pattern and/or color pattern of the LED of the light emitter 121 in comparison with the starting time point of the pressure operation according to the determined degree of pressure will be described with reference to Tables 3 and 4 below. Table 3 below shows an example of the blinking pattern of the LED in the pressure operation when the light emitter 121 is configured with one LED, but the present disclosure is not limited thereto.

TABLE 3

| | Measurement start operation | Pressure operation | Measurement development operation | Measurement completion operation |
|---|---|---|---|---|
| Pattern 1 | LED ON | Reduce LED brightness | LED blinking | LED OFF |
| Pattern 2 | LED blinking | Increase LED blinking speed | LED ON | |
| Pattern 3 | LED OFF | Increase LED brightness Increase LED blinking speed | LED ON | |
| Pattern 4 | LED OFF | Increase LED brightness | LED blinking | |

TABLE 3-continued

For example, referring to pattern 1, the LED is turned on at a first brightness in the measurement start operation, and when the pressure has reached an appropriate pressure in the pressure operation, the brightness of the LED may be reduced to a predetermined threshold value or less. Then, in the measurement development operation, the LED may be blinked while the measurement is in progress. At this time, the blinking speed of the LED may be predefined. When the measurement is complete, the LED may be turned off.

In this case, in the pressure operation, the brightness of the LED may be gradually reduced to correspond with the increase in the pressure from the starting point of the pressure. In addition, when the pressure does not reach an appropriate level within a predetermined period of time in the pressure operation, the further pressure may be guided by turning back on the LED at the first brightness. Similarly, the user may be guided with patterns 2 to 4, and various other patterns that are not exemplified herein.

Table 4 below shows the blinking pattern of the LED in the pressure operation when the light emitter 121 is configured with a plurality of LEDs having different wavelengths, but the present disclosure is not limited thereto.

TABLE 4

| | Measurement start operation | Pressure operation | Measurement development operation | Measurement completion operation |
|---|---|---|---|---|
| Pattern 1 | Wavelength 1 | Wavelength 1 →Wavelength 2 Reduce brightness of wavelength 1 | Wavelength 2 | Wavelength 1 |
| Pattern 2 | Wavelength 1 | Wavelength 1 →Wavelength 2 Reduce brightness of wavelength 1 | Wavelength 2 | Wavelength 3 |
| Pattern 3 | Wavelength 1 | Wavelength 1 →Wavelength 2 Reduce brightness of wavelength 1 | Wavelength 2 | LED OFF |

For example, referring to pattern 1, the LED having a first wavelength may be turned on in the measurement start operation, and the LED having a second wavelength may be turned on when the pressure applied reaches an appropriate level in the pressure operation. Then, in the measurement development operation, the LED having the second wavelength may be turned on while the measurement is in progress. When the measurement is complete, the LED having a third wavelength may be turned on.

At this time, in the pressure operation, the brightness of the LED having the second wavelength may be gradually increased to correspond with the increase in the pressure from the starting point of the pressure, while the brightness of the LED having the first wavelength is gradually reduced to correspond with the increase in the pressure. Also, if the pressure does not reach an appropriate level within a predetermined period of time in the pressure operation, the LED having the first wavelength may be turned back on at the same brightness as that in the measurement start operation to output a notification. Similarly, the user may be guided with patterns 2 to 4, and various other patterns that are not exemplified herein.

The processor 130 may detect a biosignal of the object by controlling the sensor part 110. In this case, the biosignal may be an antioxidant signal, but is not limited thereto. Hereinafter, for convenience of description, an antioxidant signal will be taken as an example of the biosignal. In this case, the antioxidant signal may be a signal associated with carotenoids accumulated in the epidermal layer of the skin.

For example, the processor 130 may control the light source 111 to emit light of a wavelength range of 400 nm or more and 600 nm or less, for example, light of a blue wavelength included in the absorption band of an antioxidant material (e.g., carotenoids), and the detector 112 may detect an antioxidant signal based on light scattered or reflected from the object.

When the biosignal, for example, the antioxidant signal, is received from the sensor part 110, the processor 130 may pre-process the received antioxidant signal. For example, the processor 130 may measure a hemoglobin signal by controlling the light source 111 to emit light in a green wavelength range belonging to the absorption band of hemoglobin, and may nullify the effect of materials other than the antioxidant material on the measured antioxidant signal by normalizing the antioxidant signal by subtracting the hemoglobin signal from the antioxidant signal or dividing the antioxidant signal by the hemoglobin signal.

The processor 130 may estimate the antioxidant index of the user based on the received antioxidant signal.

In this case, the processor 130 may estimate the antioxidant index of the object using an antioxidant index estimation model. Here, the antioxidant index estimation model defines the relationship between the antioxidant signal and the antioxidant index, and may be constructed in advance through regression analysis or machine learning and stored in an internal or external database of the processor 130. The antioxidant index estimation model may be constructed in the form of an equation algorithm or a matching table, but is not limited thereto.

For example, the processor 130 may control the light source 111 of the sensor part 110 to emit light having different wavelengths, then calculate the wavelength-specific absorbance based on the ratio between the measured amount of light at each wavelength and the reference amount of light, and extract a feature value using the calculated wavelength-specific absorbance. For example, the feature value may be extracted by combining the calculated wavelength-specific absorbance and correcting the baseline of a waveform. Thereafter, the processor 130 may obtain a biosignal by applying the extracted feature value to a predefined estimation model. Equations 1 to 3 below show an example of calculating the wavelength-specific absorbance and estimating the antioxidant index using the wavelength-specific absorbance.

$$A(\lambda) = -\log_{10} \frac{I_m}{I_0} \quad (1)$$

Here, $A(\lambda)$ represents the wavelength-specific absorbance, $I_m$ represents the amount of light of a specific wavelength measured at a first region of the object, and $I_0$ represents the reference amount of light obtained as a result of calibration for the specific wavelength.

$$AO = A_{\lambda 2} - \left(\frac{\lambda_3 - \lambda_2}{\lambda_3 - \lambda_1}\right) \times A_{\lambda 1} - \left(\frac{\lambda_2 - \lambda_1}{\lambda_3 - \lambda_1}\right) \times A_{\lambda 3} \quad (2)$$

Here, AO, as an example of a feature value, represents an antioxidant peak obtained by combining the wavelength-specific absorbance and correcting the baseline of a waveform. $\lambda_1$, $\lambda_2$, and $\lambda_3$ each represent a wavelength, and $A_{\lambda 1}$, $A_{\lambda 2}$, and $A_{\lambda 3}$ each represent wavelength-specific absorbance obtained through Equation 1. The length of the wavelength may be longer in order of $\lambda_1$, $\lambda_2$, and $\lambda_3$.

$$Y = a \times AO + b \quad (3)$$

Here, Y represent an antioxidant value, AO represents an antioxidant peak, and a and b represent preset values. However, Equation 3 shows an example of an antioxidant index estimation model defined as a linear function, but is not limited thereto, and may be defined as a non-linear function, such as a logarithmic function, an exponential function, or the like.

Figure 3:
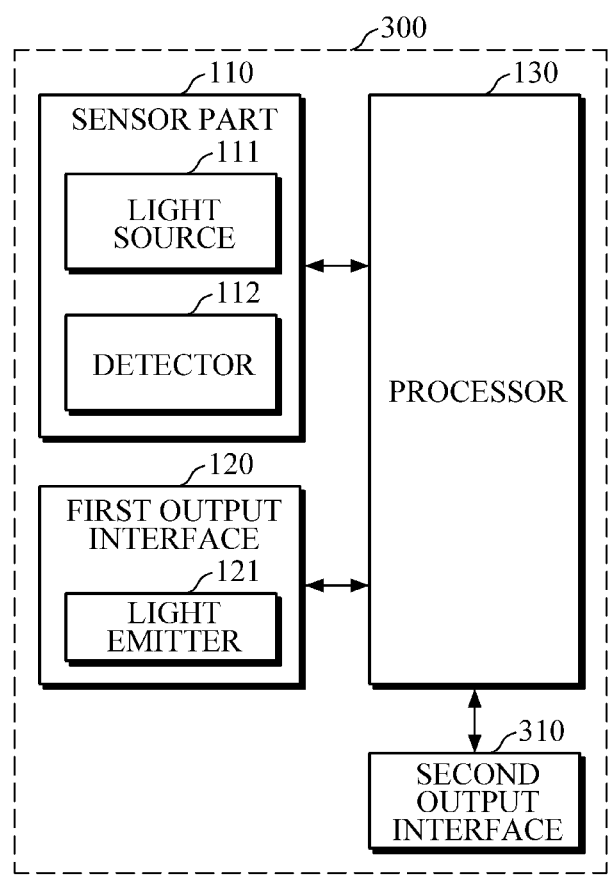
FIG. 3 is a block diagram illustrating an electronic device according to another exemplary embodiment.

FIG. 3 is a block diagram illustrating an electronic device according to another exemplary embodiment. Referring to FIG. 3, the electronic device 300 may further include a second output interface 310 in addition to the sensor part 110, the first output interface 120, and the processor 130 described above. The sensor part 100 and the first output interface 120 are described in detail with reference to FIGS. 1 to 2D, and thus the processor 130 and the second output interface 310 will be primarily described.

The second output interface 310 may be disposed on one surface of the main body of the electronic device 300. In this case, the second output interface 310 may be disposed on a different surface from that on which the sensor part 110 and the first output interface 120 are disposed. For example, the electronic device 300 is a wrist-watch type wearable device, the sensor part 110 and the light emitter 121 may be disposed on the rear surface of the watch and the second output interface 310 may be disposed on the front surface of the watch.

The second output interface 310 may be connected to the processor 130 electrically, mechanically, or through wired/wireless communication, and may output and provide the processing result of the processor 130 to the user. In this case, the second output interface 310 may provide the information to the user in various visual/non-visual manners using a display module, a speaker, and a haptic device mounted in the apparatus.

For example, the second output interface 310 may output a waveform of an antioxidant signal in a graph form. In addition, markers visually indicating a feature value obtained from the antioxidant signal, a feature value at the time of calibration to be used in the antioxidant index estimation process, and the like may be displayed.

Also, the estimated value of the user's antioxidant index may be visually displayed, wherein the estimated value may be provided to the user by using one or more of various methods, such as by changing a color, a line thickness, font, and the like based on whether the estimated value of the antioxidant index falls within or outside a normal range. Additionally, the second output interface 310 may also use vibrations and/or tactile sensations according to an abnormal antioxidant index value being estimated so that the user can easily recognize the abnormality of the antioxidant index. Alternatively, upon comparing the estimated antioxidant index value with a previous measurement history, if it is determined that the estimated antioxidant index is abnormal, the second output interface 310 may display information on a user's action to be taken, such as food information that the user should be careful about, information on a related hospital, and the like, together with a warning message, an alert signal, or the like.

For example, when the antioxidant index is less than or equal to a predetermined threshold, the processor 130 may generate recommendations for increasing the antioxidant index through the second output interface 310 and provide the recommendations to the user. For example, when the antioxidant index is less than or equal to the predetermined threshold, the second output interface 310 may provide recommendations, such as displaying text such as "eat more vegetable," "reduce smoking," "reduce alcohol intake," "exercise more," "reduce stress," and the like, to the user.

The processor 130 may control the second output interface 310 to provide the user with instructions on the guiding method of the first output interface 120 before detecting a biosignal. The method of providing the instructions by the second output interface 310 will be described with reference to FIGS. 4A to 4D.

FIGS. 4A to 4D are diagrams illustrating a second output interface according to an exemplary embodiment. FIGS. 4A to 4D illustrate an example in which the second output interface 310 provides instructions visually by outputting graphical objects, but the present disclosure is not limited thereto, such that the second output interface 310 may provide instructions in a non-visual manner by using a speaker, a haptic module, and the like as described above.

Figure 4A:
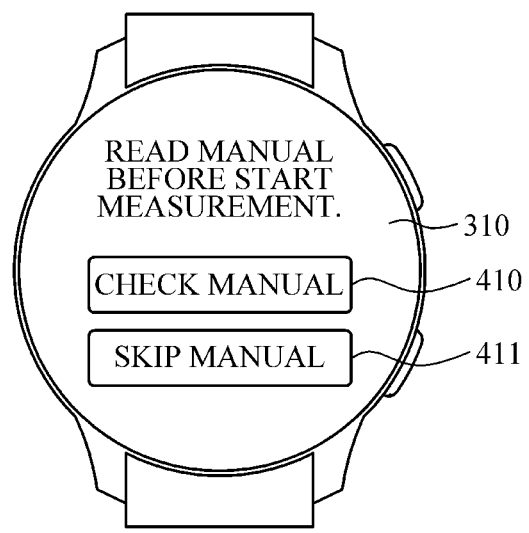
FIGS. 4A to 4D are diagrams illustrating a second output interface according to an exemplary embodiment.

Referring to FIG. 4A, the second output interface 310 may output a graphical object 410 for the user to check instructions on the guiding method of the first output interface 120, and a graphical object 411 for the user to skip the instructions.

Figure 4B:
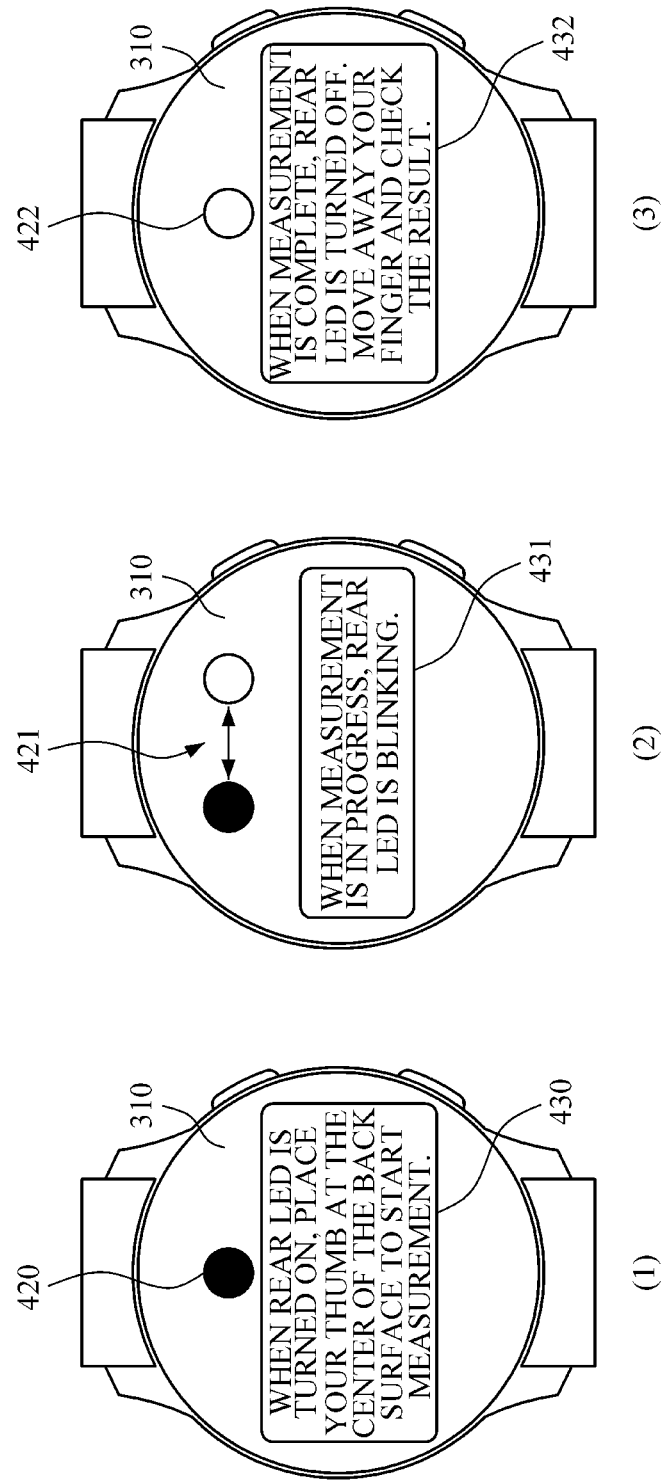
Figure 4C:
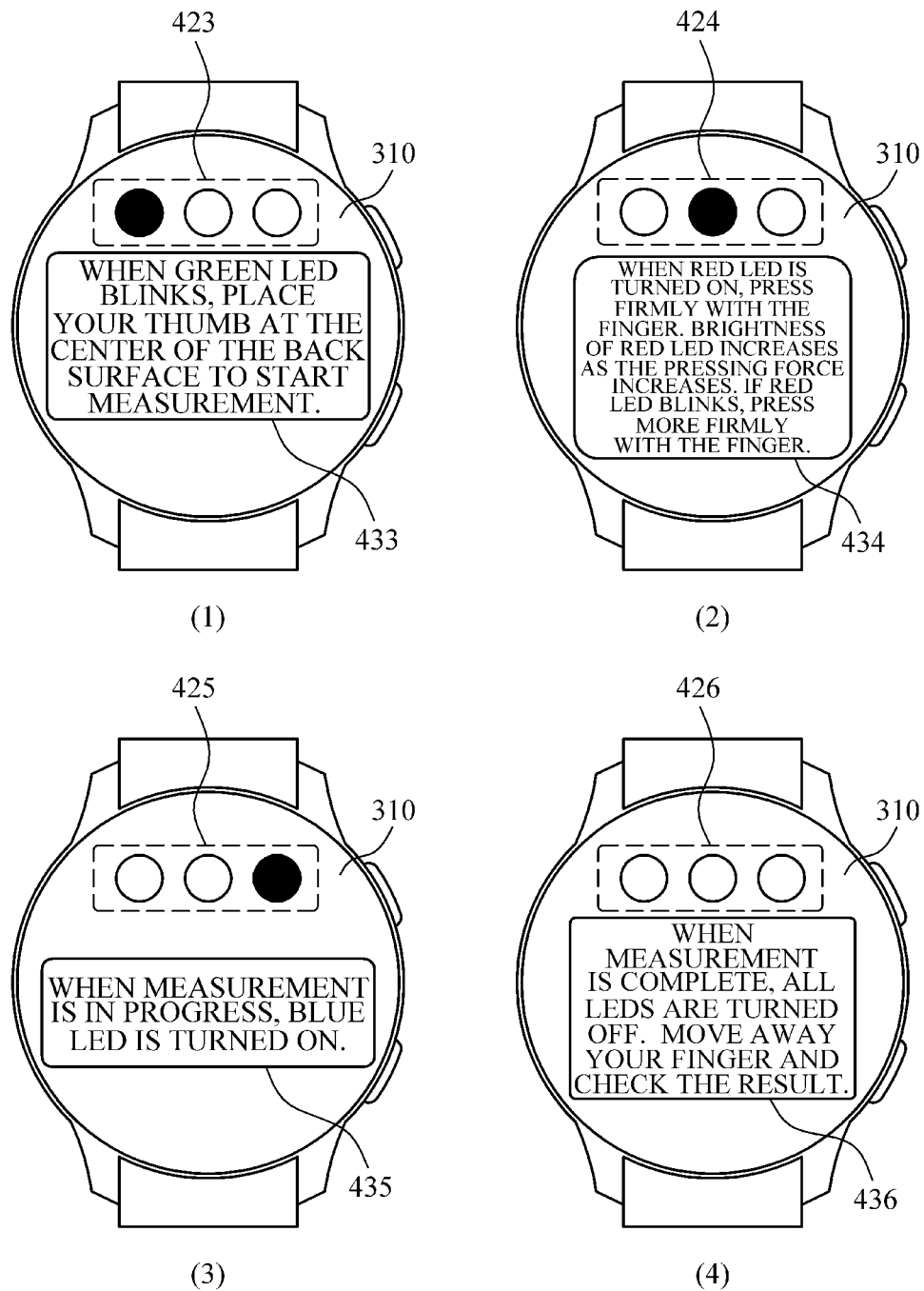

When the user selects the graphical object 410 for checking the instructions, the second output interface 310 may output graphical objects regarding explanatory information on a light-emitting mode for each operation together with the light-emitting mode of the first output interface 120 as shown in (1) to (3) of FIG. 4B, or (1) to (4) of FIG. 4C.

FIG. 4B shows an example in which the second output interface 310 provides an instruction on the guiding method of the first output interface 120 when the light emitter 121 is configured with one LED.

Referring to (1) to (3) of FIG. 4B, the second output interface 310 may output graphical objects 420, 421, and 422 for the light-emitting modes of the light emitter 121 by which the measurement start operation, the measurement development operation, and the measurement completion operation are respectively guided, and graphical objects 430, 431, and 432 for explanatory information on the light-emitting modes of each operation.

(1) to (3) of FIG. 4B illustrate the example in which the first output interface 120 turns on the LED in the measurement start operation, blinks the LED in the measurement development operation, and turns off the LED in the measurement completion operation. However, as described above, the blinking pattern of the LED for each operation is not limited thereto.

In addition, FIG. 4B illustrates an example in which the first output interface 120 does not guide the pressure operation, but the first output interface 120 may guide the pressure operation by adjusting the blinking pattern of the LED as described above in FIG. 1. A detailed description thereof will be omitted.

FIG. 4C illustrates an example in which the second output interface 310 provides instructions on the guiding method of the first output interface 120 when the light emitter 121 is configured with a plurality of LEDs having different wavelengths from each other. It is illustrated in FIG. 4C that the plurality of LEDs are separately disposed without forming a module, but the present disclosure is not limited thereto, and the plurality of LEDs having different wavelengths from each other may form one module as described above in FIG. 2C.

Referring to (1) to (4) of FIG. 4C, the second output interface 310 may output graphical objects for the light-emitting modes of the light emitter 121 by which the measurement start operation, the pressure operation, the measurement development operation, and the measurement completion operation are guided respectively, and graphical objects 433, 434, 435, and 436 for explanatory information on the light-emitting modes for each operation.

Unlike the example described in FIG. 1, in the example shown in (1) to (4) of FIG. 4C, the first output interface 120 turns on the LED having the first wavelength in the measurement start operation, turns on the LED having the second wavelength at the starting time point of the pressure operation, and increases the brightness of the LED having the second wavelength according to the degree of pressure, blinks the LED having the second wavelength in the case where the degree of pressure does not reach an appropriate pressure, turns on the LED having the third wavelength in the measurement development operation, and turns off the LED in the measurement completion operation. However, as described above, the blink pattern and color pattern of the LED for each measurement operation are not limited thereto.

In addition, (1) to (4) of FIG. 4C illustrate an example in which the first wavelength is a green wavelength, the second wavelength is a red wavelength, and the third wavelength is a blue wavelength, but the ranges of each wavelength are not limited thereto.

Figure 4D:
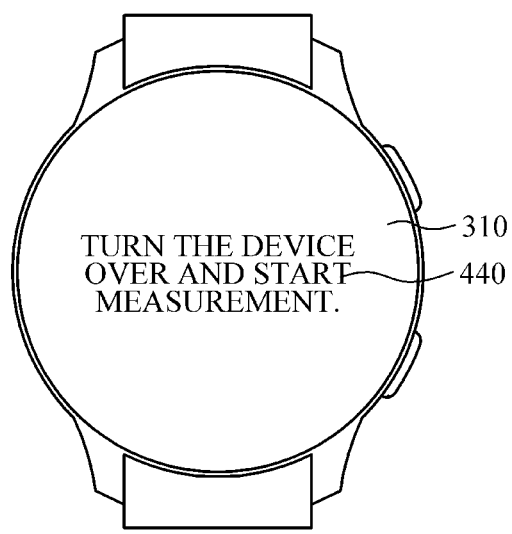

The second output interface 310 may output the graphical objects as shown in (1) to (3) of FIG. 4B, or (1) to (4) of FIG. 4C, and then, when the user selects the graphical object 411 for skipping the instructions in FIG. 4A, may output a text message 440 to guide the user to start a measurement as shown in FIG. 4D.

Figure 5:
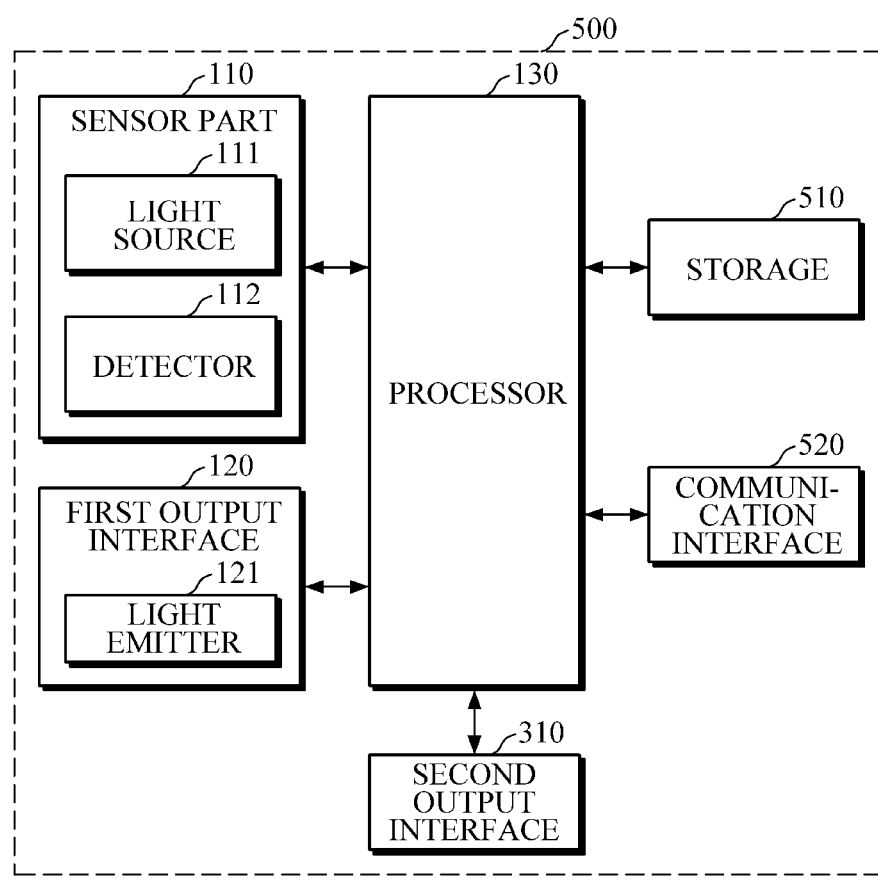
FIG. 5 is a block diagram illustrating an electronic device according to another exemplary embodiment.

FIG. 5 is a block diagram illustrating an electronic device according to another exemplary embodiment. Referring to FIG. 5, an electronic device 500 may further include a storage 510, and a communication interface 520, in addition to the configuration of the electronic device 300 described above in FIG. 3. Hereinafter, a description of the redundant portions is omitted and the storage 510 and the communication interface 520 will be described in detail.

The storage 510 may store a processing result of the sensor part 110 and/or the processor 130. For example, the storage 510 may store a detected biosignal, an estimated antioxidant index, etc. The storage 510 may store a variety of reference information necessary for antioxidant index estimation in addition to the aforementioned information. For example, the reference information may include user characteristic information, such as a user's age, gender, health condition, and the like. Also, the reference information may include information, such as an antioxidant index estimation model, antioxidant index estimation criteria, calibration cycle, reference force set for each user, and/or reference force distribution. However, the reference information is not limited thereto.

In this case, the storage 510 include at least one type of storage medium of a flash memory type, a hard disk type, a multimedia card micro type, a card type memory (for example, secure digital (SD) or extreme digital (XD) memory), a random access memory (RAM), a static random access memory (SRAM), a read-only memory (ROM), an electrically erasable programmable read-only memory (f), a programmable read-only memory (PROM), a magnetic memory, a magnetic disk, and an optical disk, but is not limited thereto.

The communication interface 520 may communicate with an external device under the control of the processor 130 using wired/wireless communication techniques and transmit and receive various types of data. For example, the communication interface 520 may transmit an antioxidant index estimation result to the external device, and receive various types of reference information necessary for antioxidant index estimation, for example, user characteristic information, such as a user's age, gender, health condition, etc., from the external device. In this case, the external device may include an information processing device, such as a smartphone, a tablet PC, a desktop computer, a notebook computer, etc.

In this case, the communication techniques may include Bluetooth communication, Bluetooth Low Energy (BLE) communication, near field communication unit, WLAN communication, ZigBee communication, infrared data association (IrDA) communication, Wi-Fi direct (WFD) communication, ultra wideband (UWB) communication, Ant+ communication, WI-FI communication, and mobile communication techniques, but are not limited thereto.

Figure 6:
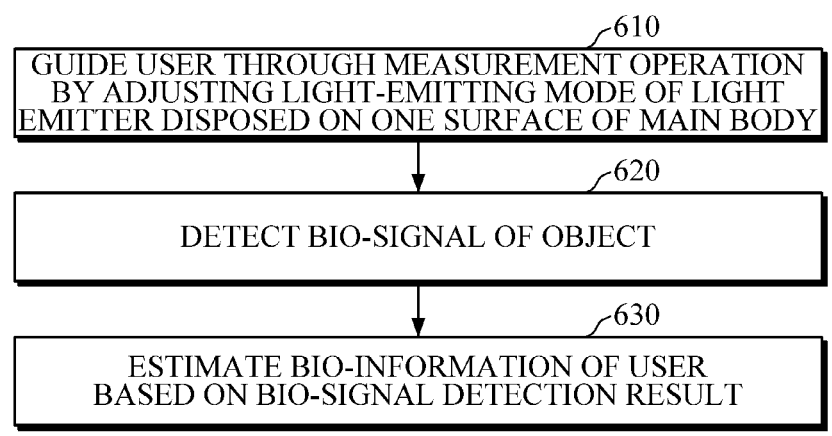
FIG. 6 is a flowchart illustrating a method of estimating bioinformation according to an exemplary embodiment.

FIG. 6 is a flowchart illustrating a method of estimating bioinformation according to an exemplary embodiment. The method of FIG. 6 may be one exemplary embodiment of a method performed by the electronic devices 100, 300, and 500 according to the exemplary embodiments of FIGS. 1, 3, and 5. The method is described in detail above and thus will be set forth in brief to avoid redundancy.

First, a user may be guided through a measurement operation by adjusting a light-emitting mode of a light emitter disposed on one surface of a main body in 610. The measurement operation may include a measurement start operation, a measurement development operation, and a measurement completion operation.

In one example, when the light emitter is configured with one LED, the blinking pattern of the LED may be adjusted in each operation. In another example, when the light emitter is configured with a plurality of LEDs having different wavelengths from each other, a blinking pattern and/or a color pattern of each LED may be adjusted in each measurement operation. A detailed description thereof will be omitted.

The measurement operation may further include a pressure operation, and when the user is guided through the pressure operation, the blinking pattern and/or color pattern of the LED may be adjusted to guide the pressure operation. A detailed description thereof will be omitted.

Then, a biosignal of an object may be detected in 620. The biosignal may be an antioxidant signal which is a signal associated with carotenoids accumulated in the epidermal layer of the skin, but is not limited thereto.

At this time, the light source included in the sensor part may be controlled to emit light of a wavelength range of 400 nm or more and 600 nm or less, for example, light of a blue wavelength included in the absorption band of an antioxidant material (e.g., carotenoids), and then an antioxidant signal may be detected based on light scattered or reflected from the object.

Then, bioinformation of the user may be estimated based on the biosignal detection result in 630. The biosignal may be an antioxidant index but is not limited thereto as described above.

In this case, the antioxidant index of the object may be estimated using an antioxidant index estimation model. Here, the antioxidant index estimation model defines the relationship between the antioxidant signal and the antioxidant index, and may be constructed in advance through regression analysis or machine learning and stored in an internal or external database of the processor. The antioxidant index estimation model may be constructed in the form of an equation algorithm or a matching table, but is not limited thereto.

Figure 7:
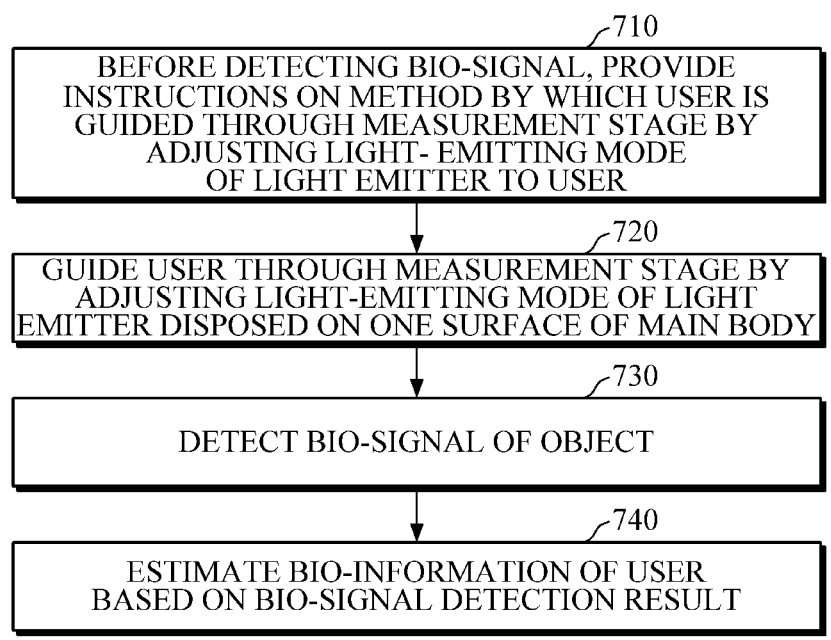
FIG. 7 is a flowchart illustrating a method of estimating bioinformation according to another exemplary embodiment.

FIG. 7 is a flowchart illustrating a method of estimating bioinformation according to another exemplary embodiment. The method of FIG. 7 may be one exemplary embodiment of a method performed by the electronic devices 100, 300, and 500 according to the exemplary embodiments of FIGS. 1, 3, and 5. The method is described in detail above and thus will be set forth in brief to avoid redundancy.

First, before a biosignal is detected, instructions on the method by which the user is guided through the measurement operation by adjusting the light-emitting mode of the light emitter may be provided to the user in 710. At this time, the instructions may be provided in various visual/non-visual manners using a display module, a speaker, a haptic device mounted in the apparatus.

In this case, when the instructions on the method by which the user is guided through the measurement operation is provided, a graphical object for the user to check the instructions on the guiding method and a graphical object for the user to skip the instructions may be output.

When the user selects a graphical object for checking the instructions, graphical objects regarding explanatory information on the light-emitting mode for each operation may be output together with the light-emitting mode of the light emitter for each operation.

The graphical objects for the light-emitting mode of the light emitter in each operation and explanatory information on the light-emitting mode for each operation may be output and then, when the user selects a graphical object for skipping instructions, a text message for guiding the user to start a measurement may be output to the user. A detailed description thereof will be omitted.

Then, the user may be guided through the measurement operation by adjusting the light-emitting mode of the light emitter disposed on one surface of the main body in 720. A detailed description thereof will be omitted.

Then, a biosignal of an object may be detected in 730. A detailed description thereof will be omitted.

Then, bioinformation of the user may be estimated based on a biosignal detection result in 740. A detailed description thereof will be omitted.

Figure 8:
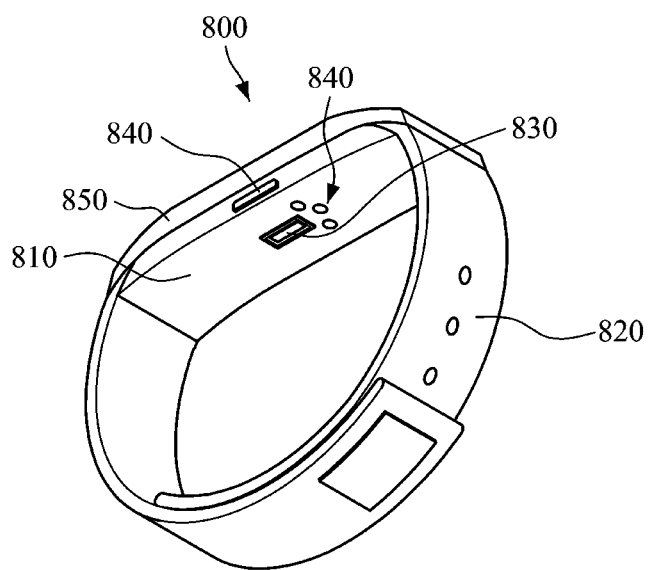
FIG. 8 is a diagram illustrating a wearable device according to an exemplary embodiment.

FIG. 8 is a diagram illustrating a wearable device according to an exemplary embodiment. A wearable device 800 may include the above-described various exemplary embodiments of the electronic devices 100, 300, and 500.

Referring to FIG. 8, the wearable device 800 may include a main body 810 and a strap 820.

The strap 820 may be connected to both ends of the main body 810 and be made of a flexible material to conform to a user's wrist. The strap 820 may include a first strap and a second strap that is separated from the first strap. One ends of the first strap and the second strap may be connected to each end of the main body 810 and may be fastened to each other using fastening means formed on the other sides thereof. In this case, the fastening means may be formed as Velcro fastening, pin fastening, or the like, but is not limited thereto. In addition, the strap 820 may be formed as one integrated piece, such as a band, which is not separated into pieces.

In this case, air may be injected into the strap 820 or an airbag may be included in the strap 820, so that the strap 820 may have elasticity according to a change in pressure applied to the wrist, and the change in pressure of the wrist may be transmitted to the main body 810.

A battery, which supplies power to the wearable device 800, may be embedded in the main body 810 or the strap 820.

Further, a sensor part 830 may be mounted on one surface of the main body 810. The sensor part 830 may include a force sensor, a PPG sensor, an impedance sensor, a motion sensor, a gyro sensor, etc. In this case, the PPG sensor may include a light source and a CIS-based image sensor.

The processor may be mounted in the main body 810. The processor may control the sensor part 830, a first output interface 840, and a second output interface 850. Also, the processor may estimate an antioxidant index based on a detected antioxidant signal. A detailed description thereof will be omitted.

The first output interface 840 may be disposed on the same surface as the sensor part 830. The first output interface 840 may include a light emitter. When the light emitter is configured with one LED, the blinking pattern of the LED may be adjusted in each operation, and when the light emitter is configured with a plurality of LEDs having different wavelengths from each other, the blinking pattern and/or the color pattern of the LEDs may be adjusted in each operation. A detailed description thereof will be omitted.

The second output interface 850 may be disposed on the front surface of the main body 810. The second output interface 850 may display an antioxidant index estimation result and provide instructions on the guiding method of the first output interface 840. A detailed description thereof will be omitted.

A storage may be included in the main body 810 and may store information processed by the processor and reference information used for antioxidant index estimation.

In addition, the wearable device 800 may include a manipulator 840 configured to receive a user's control command and transmit it to the processor. The manipulator 840 may have a function for inputting a command to turn on/off the wearable device 800.

Additionally, the wearable device 800 may include a communication interface configured to transmit and receive various types of data to and from an external device, and various modules configured to perform additional functions provided by the wearable device 800.

Figure 9:
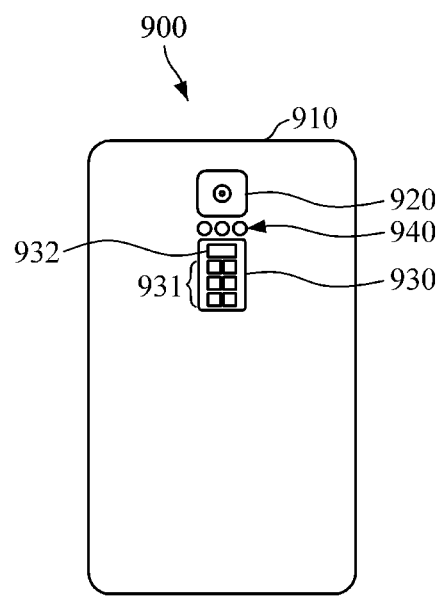
FIG. 9 is a diagram illustrating a smart device according to an exemplary embodiment.

FIG. 9 is a diagram illustrating a smart device according to an exemplary embodiment. A smart device 900 may include the above-described various exemplary embodiments of the electronic devices 100, 300, and 500. Here, the smart device may include a smartphone, a tablet PC, and the like.

Referring to FIG. 9, the smart device 900 may include a main body 910 and a sensor part 930 disposed on one surface of the main body 910. The sensor part 930 may include a light source 931 and a detector 932. In this case, the detector 932 may include a CIS-based image sensor. The sensor part 930 may be disposed on the rear surface of the main body 910 as illustrated, but is not limited thereto. Also, the sensor part 930 may include an auxiliary sensor, such as an impedance sensor, a motion sensor, or the like.

A processor may be mounted in the main body 910, may control a first output interface 940 and a second output interface (not shown), and may estimate an antioxidant index based on a detected antioxidant signal. A detailed description thereof will be omitted.

Meanwhile, an image sensor 920 may be mounted in the main body 910 as illustrated, and the image sensor 920 may capture an image of an object, for example, a finger, when the user approaches the finger to the sensor part 930 to measure a biosignal and may transmit the image to the processor. In this case, the processor may identify a relative position of the finger relative to the actual position of the sensor part 930 and provide the user with a graphical object regarding information on the relative position of the finger through the second output interface.

In addition, a storage, a communication interface, and the like may be mounted in the main body 810, whereby an antioxidant index estimated by the processor may be stored or may be transmitted to other external devices. In addition, various modules configured to perform various functions may be mounted in the main body 910.

The current embodiments can be implemented as computer readable codes in a computer readable record medium. Codes and code segments constituting the computer program can be easily inferred by a skilled computer programmer in the art. The computer readable record medium includes all types of record media in which computer readable data are stored. Examples of the computer readable record medium include a ROM, a RAM, a CD-ROM, a magnetic tape, a floppy disk, and an optical data storage. Further, the record medium may be implemented in the form of a carrier wave such as Internet transmission. In addition, the computer readable record medium may be distributed to computer systems over a network, in which computer readable codes may be stored and executed in a distributed manner.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An electronic device comprising:
a main body;
a sensor part disposed at one surface of the main body and configured to detect a light signal of an object;
a first output interface comprising a light emitter disposed at the one surface of the main body and configured to guide a user through a measurement operation by controlling a light-emitting mode of the light emitter, the measurement operation comprising a measurement start operation, a measurement development operation, a measurement completion operation, and a pressure operation, the pressure operation being an operation between the measurement start operation and the measurement development operation in which the object presses the sensor part; and a processor configured to control the light emitter according to the measurement operation and estimate user bioinformation based on a result of detecting the light signal by the sensor part, wherein the processor is further configured to determine a degree of pressure based on a force with which the object presses the sensor part, wherein the processor is further configured to guide the measurement operation by adjusting the light-emitting mode of the light emitter in comparison with a starting time point of the pressure operation based on the degree of pressure, and wherein the processor is further configured to determine the degree of pressure by the user based on a change in absorbance at a predetermined wavelength range.

2. The electronic device of claim 1, wherein, when the light emitter is configured with one light emitting diode (LED), the first output interface is configured to adjust a blinking pattern of the LED of the measurement operation.

3. The electronic device of claim 1, wherein, when the light emitter is configured with a plurality of LEDs having different wavelengths, the first output interface is configured to adjust at least one of a blinking pattern or a color pattern of each of the plurality of LEDs in the measurement operation.

4. The electronic device of claim 1,
wherein during the pressure operation, the controller is further configured to guide the user by adjusting at least one of a blinking pattern or a color pattern of an LED in the light emitter.

5. The electronic device of claim 1, wherein the first output interface is further configured to guide the measurement operation by adjusting at least one of a blinking speed, brightness, color type, or color density of the LED in comparison with the starting time point of the pressure operation according to the determined degree of pressure.

6. The electronic device of claim 1, wherein the processor is further configured to determine whether the determined degree of pressure reaches a level of pressure, and the first output interface, when the processor determines that the degree of pressure does not reach the level of pressure, is further configured to guide the user through additional pressure by increasing a blinking speed of the LED, increasing brightness of the LED, adjusting color of the LED, or increasing density of color of the LED.

7. The electronic device of claim 1, wherein the sensor part comprises a light source configured to emit light toward the object and a detector configured to detect a light signal based on light scattered or reflected from the object, wherein a wavelength of the light emitted by the light source is 400 nm or more and 600 nm or less and the user bioinformation is an antioxidant index.

8. The electronic device of claim 1, further comprising a second output interface disposed on another surface of the main body and configured to provide instructions on a guiding method of the first output interface to the user before the light signal is detected.

9. The electronic device of claim 8, wherein the second output interface is further configured to output graphical objects regarding explanatory information on a light-emitting mode for each operation together with the light-emitting mode of the first output interface for each operation.

10. The electronic device of claim 8, wherein the second output interface is further configured to output a graphical object for the user to skip the instructions and output a text message for guiding the user to start a measurement when the user selects the graphical object.

11. The electronic device of claim 1, wherein when the light emitter comprises one light emitting diode (LED), the controller is further configured to:
during the measurement completion operation, turn the LED on, during the measurement development operation, control the LED to blink, and during the measurement completion operation, turn the LED off;
during the measurement completion operation, control the LED to blink, during the measurement development operation, turn the LED on, and during the measurement completion operation, turn the LED off;
during the measurement completion operation, control the LED to be off, during the measurement development operation, turn the LED on, and during the measurement completion operation, turn the LED off; or
during the measurement completion operation, control the LED to be off, during the measurement development operation, control the LED to blink, and during the measurement completion operation, turn the LED off.

12. A method of estimating bioinformation comprising:
guiding a user through a measurement operation by adjusting a light-emitting mode of a light emitter disposed at one surface of a main body, the measurement operation comprising a measurement start operation, a measurement development operation, a measurement completion operation, and a pressure operation, the pressure operation being an operation between the measurement start operation and the measurement development operation in which an object presses a sensor part of the main body;
detecting a light signal of the object; and
estimating bioinformation of the user based on a result of detecting the light signal,
wherein the guiding the user through a measurement operation comprising:
determining a degree of pressure based on a force with which the object presses the sensor part;
adjusting the light-emitting mode of the light emitter in comparison with a starting time point of the pressure operation based on the degree of pressure; and determining the degree of pressure by the user based on a change in absorbance at a predetermined wavelength range.

13. The method of claim 12, wherein the guiding of the user through the measurement operation comprises, when the light emitter is configured with a single LED, adjusting a blinking pattern of the LED in the measurement operation.

14. The method of claim 12, wherein the guiding of the user through the measurement operation comprises, when the light emitter is configured with a plurality of LEDs having different wavelengths from each other, adjusting at least one of a blinking pattern or a color pattern of each of the plurality of LEDs in the measurement operation.

15. The method of claim 12,
wherein the during the pressure operation, the guiding of the user through the measurement operation comprises adjusting at least one of a blinking pattern or a color pattern of an LED in the light emitter.

16. The method of claim 12, wherein the guiding of the user through the measurement operation comprises guiding the measurement operation by adjusting at least one of a blinking speed, brightness, color type, or color density of the LED in comparison with the starting time point of the pressure operation according to the determined degree of pressure.

17. The method of claim 12, further comprising providing instructions on a method of guiding the user through the measurement operation by adjusting a light-emitting mode of the light emitter to the user before detecting the light signal.

18. The method of claim 17, wherein the guiding of the user through the measurement operation comprises outputting a graphical object for the user to skip the instructions and outputting a text message for guiding the user to start a measurement when the user selects the graphical object.

19. The method of claim 12, wherein when the light emitter comprises one light emitting diode (LED), and
   wherein the guiding the user through the measurement operation by adjusting a light-emitting mode of the light emitter disposed at one surface of a main body comprises:
   during the measurement completion operation, turning the LED on, during the measurement development operation, controlling the LED to blink, and during the measurement completion operation, turning the LED off;

during the measurement step-completion operation, controlling the LED to blink, during the measurement development operation, turning the LED on, and during the measurement completion operation, turning the LED off;

during the measurement completion operation, controlling the LED to be off, during the measurement development operation, turning the LED on, and during the measurement completion operation, turning the LED off; or during the measurement completion operation, controlling the LED to be off, during the measurement development operation, controlling the LED to blink, and during the measurement completion operation, turning the LED off.

* * * * *